United States Patent
Etminan

(10) Patent No.: US 10,245,080 B2
(45) Date of Patent: Apr. 2, 2019

(54) SYSTEM FOR MOUNTING OF A CERVICAL PLATE TO A VERTEBRA

(71) Applicant: Mohammad Etminan, Houston, TX (US)

(72) Inventor: Mohammad Etminan, Houston, TX (US)

(*) Notice: Subject to any disclaimer, the term of this patent is extended or adjusted under 35 U.S.C. 154(b) by 660 days.

(21) Appl. No.: 14/730,363

(22) Filed: Jun. 4, 2015

(65) Prior Publication Data

US 2016/0331414 A1    Nov. 17, 2016

Related U.S. Application Data

(60) Provisional application No. 62/007,566, filed on Jun. 4, 2014, provisional application No. 62/137,399, filed on Mar. 24, 2015.

(51) Int. Cl.
*A61B 17/70* (2006.01)
*A61F 2/44* (2006.01)

(52) U.S. Cl.
CPC ......... *A61B 17/7059* (2013.01); *A61F 2/442* (2013.01); *A61F 2/4455* (2013.01)

(58) Field of Classification Search
CPC ...... A61B 17/7059; A61F 2/442–2/447; A61F 2002/443–2002/4495
See application file for complete search history.

(56) References Cited

U.S. PATENT DOCUMENTS

| | | | |
|---|---|---|---|
| 6,193,721 B1 | 2/2001 | Michelson | 606/70 |
| 2005/0261690 A1* | 11/2005 | Binder | A61B 17/1728 606/295 |
| 2006/0167456 A1 | 7/2006 | Johnston et al. | 606/86 B |
| 2007/0270965 A1* | 11/2007 | Ferguson | A61B 17/7059 623/17.11 |
| 2008/0300634 A1* | 12/2008 | Gray | A61B 17/7059 606/280 |
| 2010/0057128 A1* | 3/2010 | Bullard | A61B 17/7059 606/246 |
| 2012/0179207 A1 | 7/2012 | Mekhail et al. | 606/281 |
| 2013/0345814 A1* | 12/2013 | Walkenhorst | A61F 2/4465 623/17.16 |

OTHER PUBLICATIONS

International Search Report dated Jun. 23, 2016 issued in corresponding PCT International Application No. PCT/US2016/023740.

* cited by examiner

*Primary Examiner* — Ellen C Hammond
*Assistant Examiner* — Tessa M Matthews
(74) *Attorney, Agent, or Firm* — Ostrolenk Faber LLP

(57) ABSTRACT

A system that includes a cervical plate and an intervertebral cage, the cervical plate having a mounting section that renders the cervical plate mountable to a reference feature located on the front wall of the intervertebral cage, the reference feature being positioned to set a distance between an eyelet of the cervical plate and an edge of the front wall to position the eyelet over a mounting location on a vertebra when the mounting section is mounted to the reference feature.

7 Claims, 14 Drawing Sheets

Lateral View

Lateral View

SYSTEM FOR MOUNTING OF A CERVICAL PLATE TO A VERTEBRA

CROSS-REFERENCE TO RELATED APPLICATIONS AND CLAIM OF PRIORITY

This application claims priority to U.S. provisional application Ser. No. 62/007,566, filed Jun. 4, 2014 and U.S. provisional application Ser. No. 62/137,399, filed Mar. 24, 2015, both entitled System For Mounting Of A Cervical Plate To A vertebra. The contents of both provisional applications are hereby incorporated by reference.

FIELD OF INVENTION

Disclosed below is a novel concept for a cervical plate mounting system.

BACKGROUND AND SUMMARY OF INVENTION

One of the main issues with cervical plating systems available today is that the plate is placed onto the vertebral body in a "free hand" technique where essentially the surgeon determines where the plate should go based on anatomical reference points such as the interbody device just placed to obtain a fusion, the inferior (caudal) endplate of the cephalad vertebral body, the superior endplate of the caudad vertebral body, the disc above the surgical site and the disc below the surgical site. The optimal placement of the plate and screw is as close to the inferior border of the superior vertebral body, the superior end plate of the inferior vertebral body, and as far as possible from the disc above and the disc below although there is some variation on surgeon preferences.

Proximity to the end plates allows for better bone quality and distance from the discs above and below allows for preventing damage to those discs. Thus, ideal or perfect plate placement can be very important to a successful operation.

The land marks mentioned above may be easily seen on a saw bone. However, during surgery the presence of limited exposure, presence of blood, limited visualization of the end plates due to plate design, and inability to see the disc above and below due to lack of sufficient visual variability makes free hand placement difficult.

In conventional procedure, temporary fixation pins are often used to allow for holding the plate in position while a more exact determination of the location and alignment of the plate is performed. However, these pins are often quite small in diameter allowing the plate to move around the pin. Also variation in bone anatomy and texture sometimes results in the pin "sliding" and not entering the bone of the vertebral body in the intended position thus compromising the position.

All these difficulties add to the complexity of an operation and make the result less reproducible from patient to patient and operation to operation.

There are cervical plate/cage designs that are available that mate the cage to the plate. However, these systems only work with one level procedures and cannot be used for multilevel designs if the surgeon chooses to use a multilevel or single level plate with two screws in each vertebral body.

A system according to the present invention allows for solving all the above mentioned problems. By providing a cage that has a screw insertion hole or fixation point at a fixed distance from its top edge, for example, a system according to the present invention gives the surgeon a fixed reference point based on which the plate can be referenced and permanent bone screw positions may be located and drilled. The cage can be manufactured so that the reference hole is a fixed distance from, for example, the top of the cage, which in turn makes it a fixed distance from the inferior endplate (or superior endplate depending on the orientation of the cage) regardless of the height of the cage. Because this distance is fixed, a system of either a cervical plate or a drill guide for any cervical plate that references off of the hole in the cage will allow for the perfect positioning of the cervical plate in relationship to discs above and below and the superior and inferior endplates every time. The reference point on the cage also allows for the usage of a very stable fixation mechanism that allows for easier control of the cervical plate before it is definitively fixed to a vertebra with a screw or screws. A version of the present invention will allow for adjustment of plate position in relation to the fixation point to allow for optimal plate fixation and position.

A system according to the present invention will also allow for measurement of length of a plate necessary via calipers. This task of length selection is another task that is presently done "free hand" by trial and error.

The cage/plate system can be used as a dedicated system that mate with each other or the cage can be used with any cervical plate system that has a drill guide specifically designed for attachment to a cage and positioning.

Alternatively specific plate holders can be designed that temporarily hold the plate to the cage and then removed after the plate is screwed definitively into position by screws into the vertebra.

A system according to the present invention can be used with a one level cervical plate or a multilevel cervical plate without modification.

The modification for the plate is the concept of adding a hole or connection mechanism on the cephalad top side of the cervical plate on at least one end or both ends of the plate that can mate to a cage configured to provide the necessary predetermined distance for an ideal location of mounting holes. This modification can be done to any plate with any locking mechanism.

The connection between the cervical plate and the cage is removed once the plate is attached to the vertebras with the definitive screws. A version can be envisioned that the connection is not removed.

DETAILED DESCRIPTION

Figure 1A:
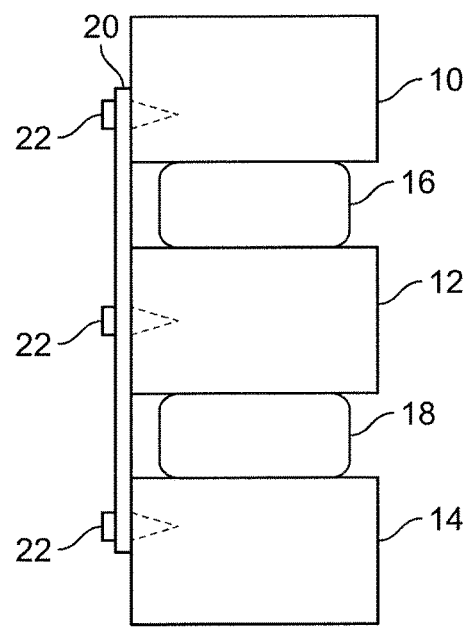
FIG. 1A depicts a side plan view of a cervical plate assembled onto a group of vertebras with intervertebral cages located between the adjacent vertebras according to the prior art.
Figure 1B:
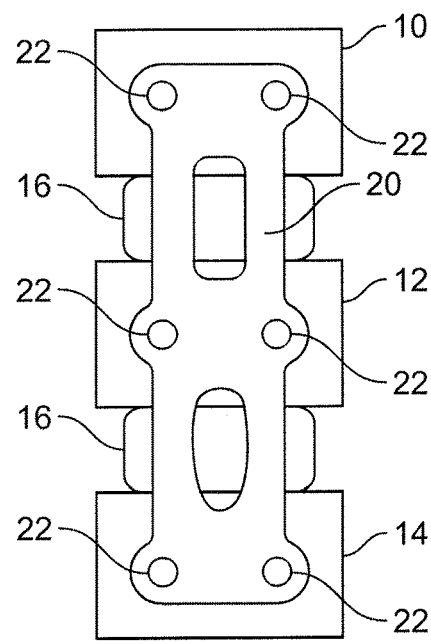
FIG. 1B depicts a front plan view of a cervical plate assembled onto a group of vertebras with intervertebral cages located between the adjacent vertebras according to the prior art.

FIGS. 1A and 1B disclose vertebras 10, 12, 14, intervertebral cages 16, 18 installed between vertebras 10, 12 and vertebras 12, 14, respectively and a cervical plate 20 coupled/mounted to vertebras 10, 12, 14 with screws 22. A typical cervical plate 20 is a metallic web having a plurality of eyelets each for receiving a respective screw 22.

To install a cervical plate 20, a surgeon estimates the proper position of plate 20 after cages 16, 18 are placed between vertebras 10, 12, 14. Thus, the result of an operation can vary from patient to patient, surgeon to surgeon, and operation to operation. A typical cervical plate may include an eyelet for temporary installation while the surgeon estimates proper positions for screws 22.

As explained above ideal positioning of a cervical plate can lead to better results. Thus, a system according to the present invention is devised to lead to the ideal positioning of a cervical plate.

A system according to the present invention may include a cage configured to provide a reference position and a cervical plate configured to register with the reference position of the cage.

A system according to the present invention may include at least one cage configured to provide a reference position, a cervical plate, a drill guide, a cannula, and a fixation component to position the drill guide relative to the cage.

A system according to the present invention may include at least one cage configured to provide a reference position, a cervical plate with a fixation component to position the cage relative to the plate.

Figure 2A:
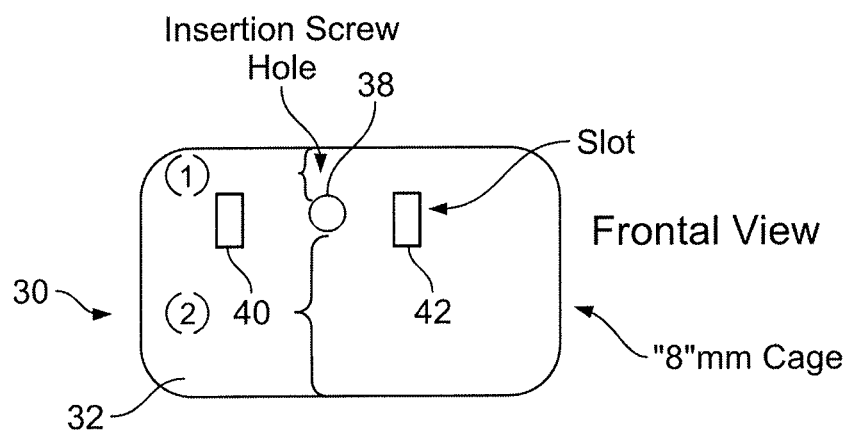
FIG. 2A depicts a front plan view.
Figure 2B:
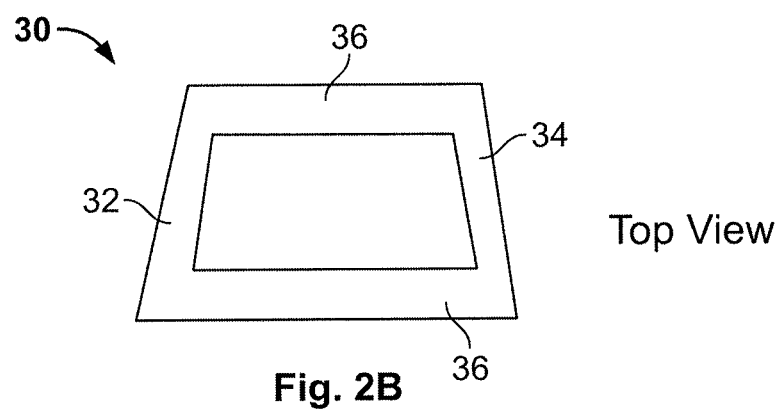
FIG. 2B depicts a top plan view.
Figure 2C:
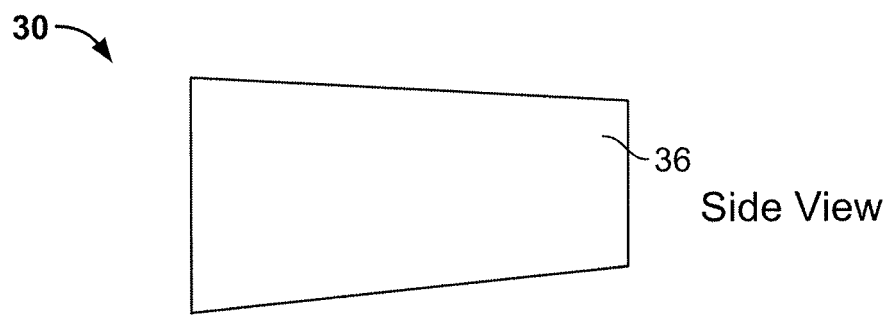
FIG. 2C depicts a side plan view of an intervertebral cage used in a system according to the present invention.

Referring to FIGS. 2A, 2B and 2C, a cage 30 for a system according to the present invention would include a front wall 32, a back wall 34, and two side walls 36 connecting front wall 32 and back wall 34 to define a space for receiving, for example, bone graph material. Front wall 32 would include an insertion screw hole 38, a first slot 40 spaced laterally from screw hole 38, and a second slot 42 spaced laterally from screw hole 38 opposite first slot 42.

A cage for a system according to the present invention can be made of any suitable bio-compatible material such as PEEK, allograft, a bio-compatible metal, a bio-compatible composite (e.g. a carbon-fiber-based composite) or the like.

Figure 2D:
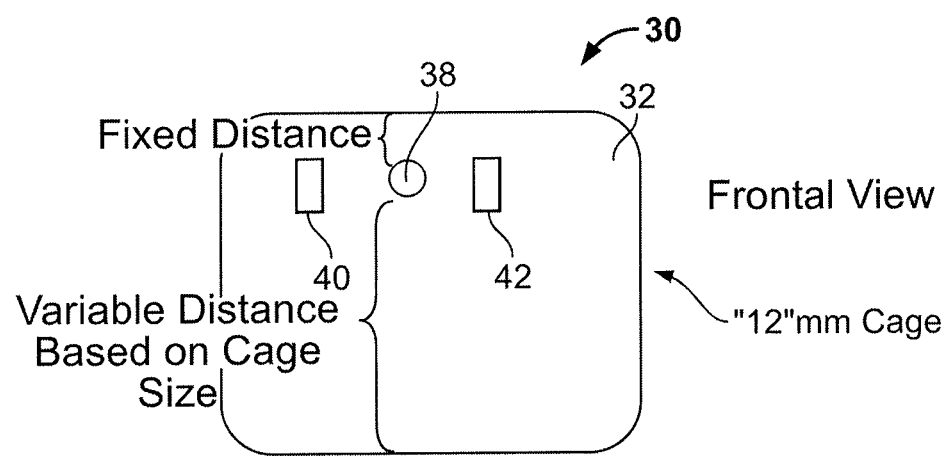
FIG. 2D depicts a front plan view of another intervertebral cage that can be used in a system according to the present invention.

According to the present invention, screw hole 38, and slots 40, 42 are located a predetermined distance from an edge (e.g. top edge) of front wall 32 to serve as referencing features as explained below. Note that FIG. 2A shows, for example, an 8 mm cage. FIG. 2D shows front wall 32 of, for example, a 12 mm cage. According to an aspect of the present invention, regardless of the height of front wall 32, the predetermined distance of the referencing features (38, 40, 42) would remain the same.

Figure 3A:
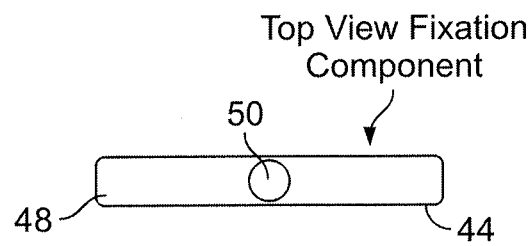
FIG. 3A depicts a top view and FIG. 3B depicts a side view of a fixation component used in a system according to the present invention.
Figure 3B:
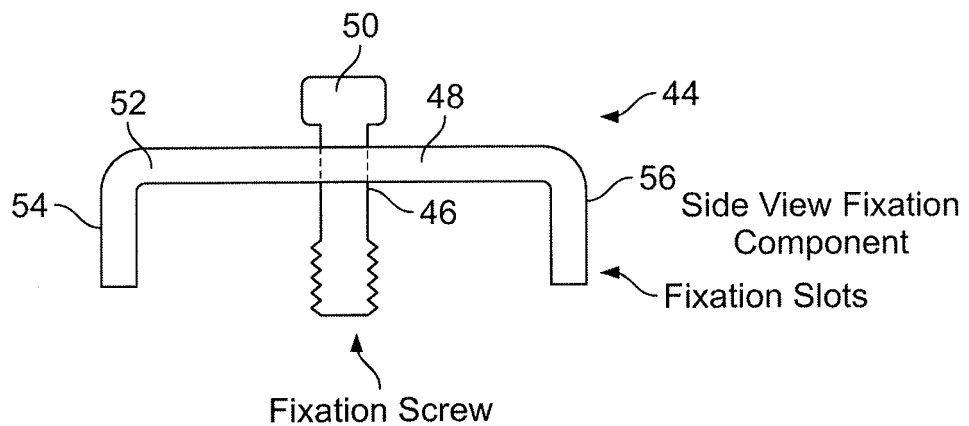

Referring now to FIGS. 3A and 3B, fixation component 44 includes a fixation screw 46 rotatably mounted in an anchor 48. Fixation screw 46 may include a knob 50 or the like feature that can allow the surgeon to rotate screw 46.

Anchor 48 includes an elongated bar 52 in which fixation screw 46 is rotatably mounted. Elongated bar 52 includes two anchors portions 54, 56 each extending in the direction of fixation screw 46. Each anchor portion 54, 56 is sized and shaped to be received in a respective slot 40, 42 to frictionally couple with front wall 32 with little or no play.

It should be noted that presence of slots 40, 42 is not required, but is considered a useful option to provide further stability. When a cage is provided that does not include slots 40, 42, features that engage slots 40, 42 may be omitted from the fixation compound 44. Alternatively, elongated bar 52 may be extended so that anchor portions 54, 56 can grip the side walls of the cervical plate in order to stabilize fixation component 44 during the operation.

Figure 3C:
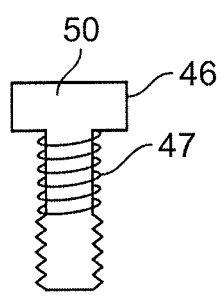
FIG. 3C depicts a fixation screw with an integrated spring.

In an alternative embodiment, as illustrated in FIG. 3C, fixation screw 46 may be integrated with a spring 47 that is connected, preferably, at one end thereof to knob 50, and can bias fixation screw 46 against a surface. Spring 47, as illustrated, could be disposed around the stem of fixation screw 46.

Figure 3D:
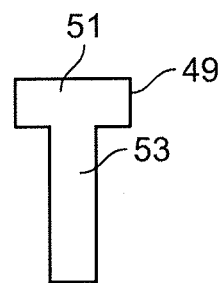
FIG. 3D depicts a fixation pin.

In yet another alternative embodiment, as illustrated in FIG. 3D, fixation screw 46 could be replaced with a pin 49, which has a head 51 and stem 52.

Figure 4:
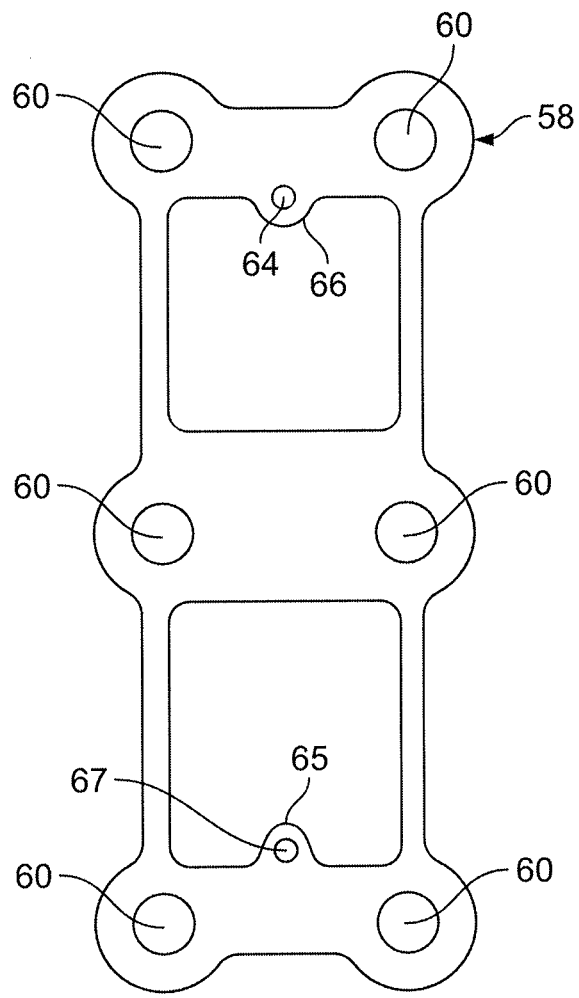
FIG. 4 depicts a front plan view of a cervical plate that can be used in a system according to the present invention.
Figure 5:
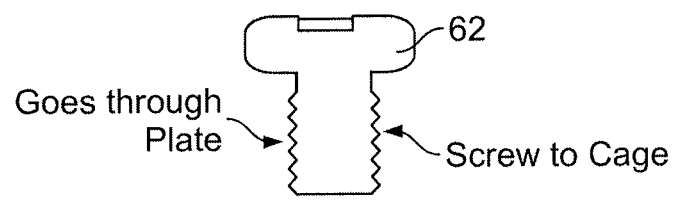
FIG. 5 is a side plan view of a screw that be used to mount a cervical plate to a vertebra.

Referring to FIG. 4, a cervical plate 58 for a system according to the present invention is made, preferably, of a suitable metallic material (or any other suitable material) and includes a plurality of eyelets 60 each for receiving a respective screw 22 (FIG. 5A) for permanent fixation of plate 58 to vertebras. Cervical plate 58 further includes an eyelet 64, which may be defined in a projecting tab 66. Eyelet 64 is located below top eyelets 60 of cervical plate 58. The distance between top eyelets 60 and eyelet 64 is selected to realize an ideal location for drilling holes into a vertebrae using referencing features (38,40,42). That is, distance between the top eyelet 60 and eyelet 64 is selected to realize an ideal location for drilling holes into a vertebrae through eyelet 60 once the plate is fixated to cage 32 via fixation devices 62, 46, or 49 through eyelet 64 into hole 38.

Figure 6:
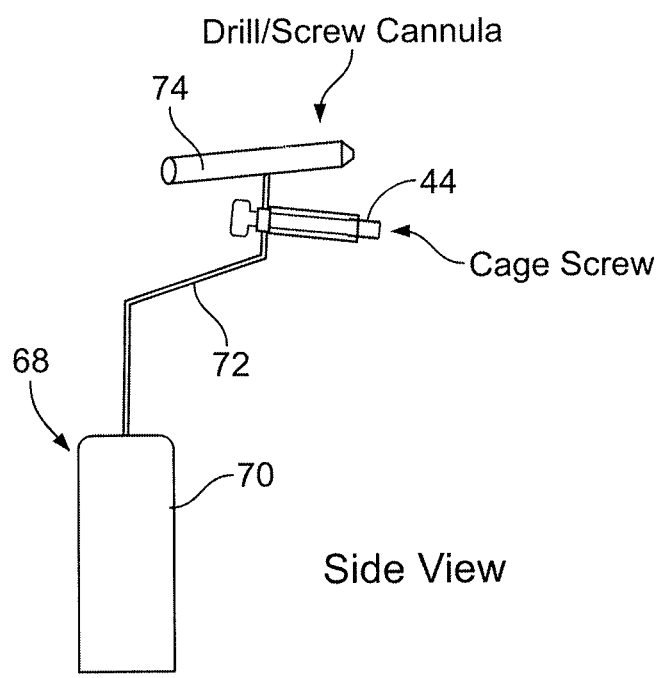
FIG. 6 depicts a side view of a drill guide having a fixation component and a cannula mounted thereon for use with a system according to the present invention.
Figure 7:
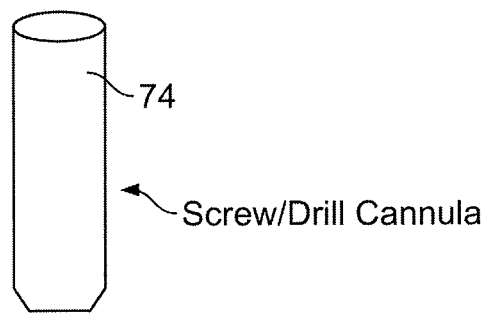
FIG. 7 depicts a cannula that may be used with a system according to the present invention.

Referring now to FIG. 6, a drill guide 68 for a system according to the present invention includes a handle 70 and a support 72, which may be a rod or the like body. Support 72 may have at least one cannula 74 (see FIG. 7) mounted preferably at its end. Cannula 74 may be a pipe or the like body having an interior dimension devised to receive a drill bit and to guide the drill bit to a site on a vertebra for defining a hole to receive a screw 62. Cannula 74, for example, may have an outside diameter so that it may mate (frictionally couple) with the inner diameter of eyelet 60. Cannula 74 may also be modified to accept the bone screw as well.

Support 72 is further configured to support a fixation component 44 at a location below cannula 74.

Figure 8:
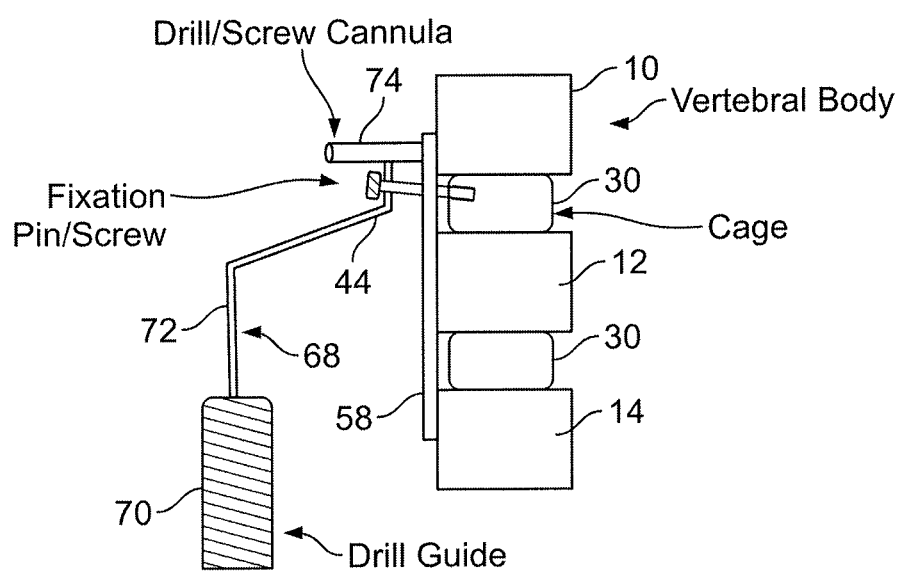
FIG. 8 depicts, viewed from the side, a step in the assembly of a cervical plate onto a group of vertebras using a system according to the present invention.
Figure 9:
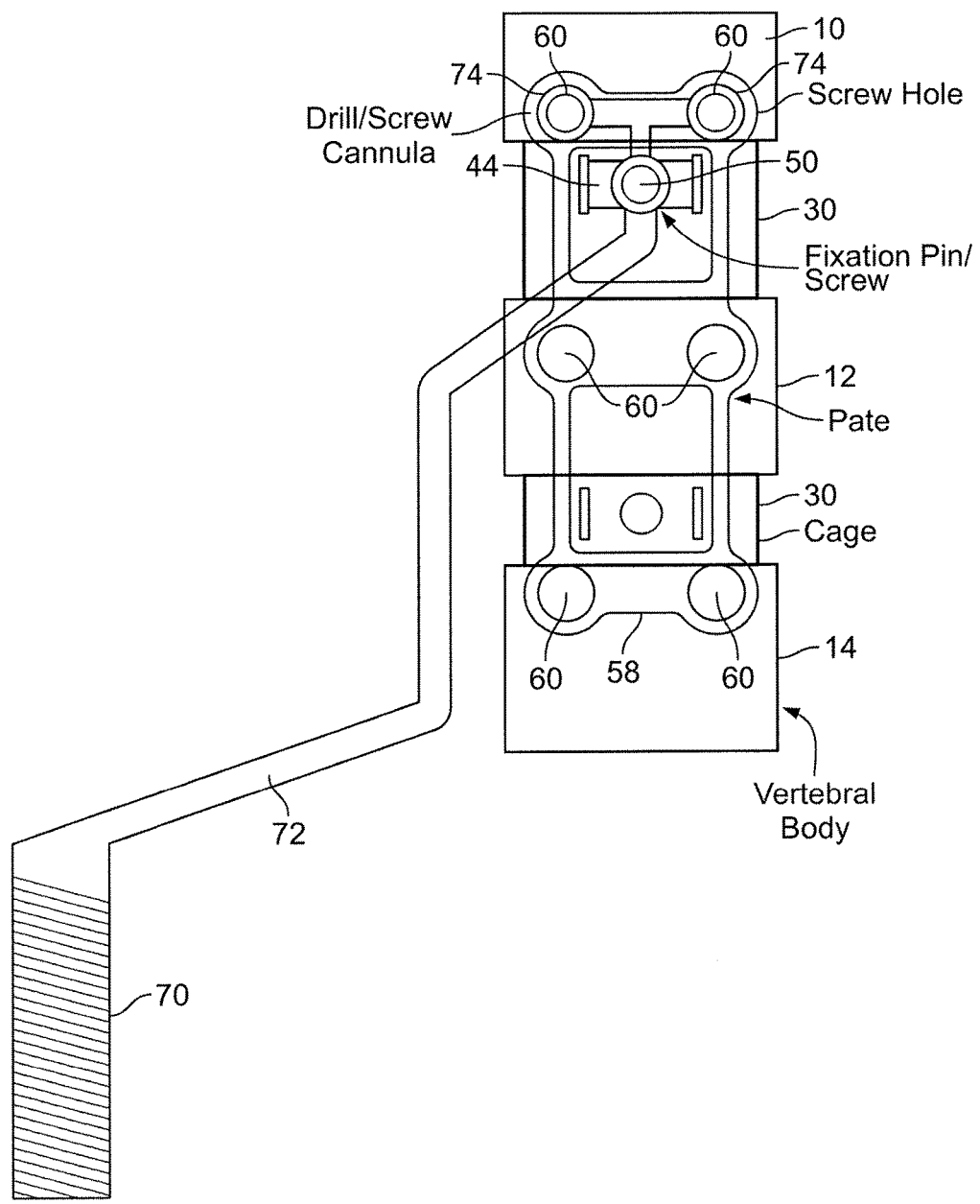
FIG. 9 depicts a front view of a step in the assembly of a cervical plate onto a group of vertebras using a system according to the present invention.
Figure 10A:
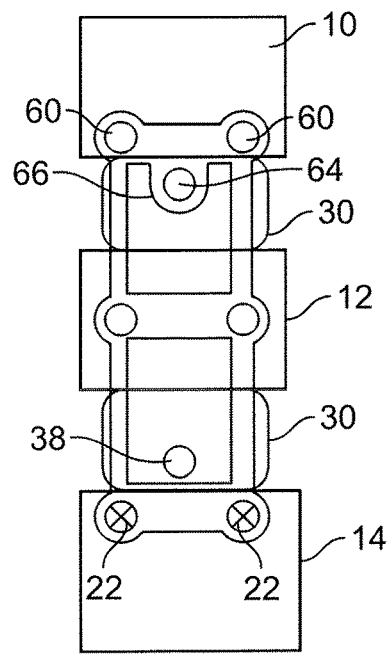
FIG. 10A depicts a front view of a cervical plate assembled, using a system according to the present invention, onto a group of adjacent vertebras supported by intervertebral cages.
Figure 10B:
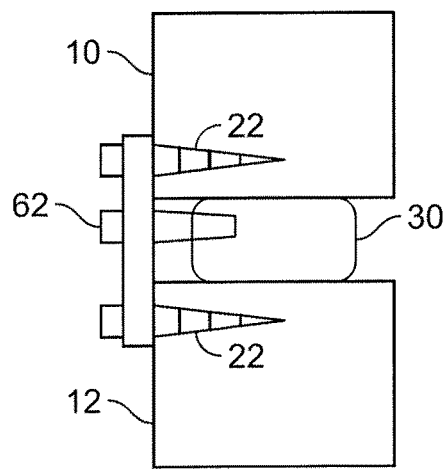
FIG. 10B illustrates a side plan view of a cervical plate assembled, using a system according to the present invention, onto two adjacent vertebras supported by an intervertebral cage.

Referring now to FIGS. 8 and 9, after a cage 30 is positioned between for example, top and middle vertebras 10, 12, a plate 58 is positioned so that eyelet 64 registers with insertion hole 38 on a front wall 32. Thereafter, fixation screw 46 is screwed into eyelet 64 and insertion hole 38 until anchor portions 54, 56 are received in slots 40, 42 and cannula 74 is registered (aligns) with a top eyelet 60 of cervical plate 58. Once cannula 74 is aligned with a top eyelet 60, and preferably mates with eyelet 60, a hole may be drilled by inserting the drill bit through cannula 74 and eyelet 60, with which it is aligned. It should be apparent that two cannulas 74 may be supported by support 72 each aligned with a respective top eyelet 60 (see FIG. 9). After holes are drilled into a vertebra (e.g. top vertebra 10), plate 58 is mounted first by screw 22 inserted into the top eyelet 60 through the attached cannula. Once the plate is fixated to the vertebral body, then fixation component 44 is disengaged and drilling guide 68 is removed. Thereafter, holes may be drilled in other vertebras 12, 14 through middle and bottom eyelets 60 of plate 58, and plate 58 further screwed to vertebras 12, 14 with screw 22.

In an alternative embodiment, a fixation component may be used without anchor portions 54,56. This embodiment may be used with a cage 30 that does not include slots 40,42. In this embodiment, fixation screw 46 may abut tab 66 and push the plate against a vertebral body so that plate 58 will be held in place, and cannulas 74 will be aligned with eyelets 60 as described. Then, plate 58 may be secured to the vertebral body with screws, with or without pre-drilling, using cannulas 74 as guides. In this embodiment, for example, cannulas 74 will be disposed around eyelets 60 and may abut the surface around eyelets 60 which would allow entry of screws into cannulas 74 with heads larger than eyelets 60.

Alternatively, plate 58 may be screwed to cage 30 between top and middle vertebras 10, 12 with a fixation screw 46 alone (without the rest of the fixation component). Fixation screw 46 may be inserted in eyelet 64 and insertion hole 38 without using drill guide 68. In this case, fixation screw 46 may have a knob 50 or a head larger than eyelet 64 so that it can be used to push tab 66 toward cage 30 until at least plate 58 makes contact with a vertebral body. Alternatively, an intermediate body, such as a washer, could be used to enable screw 46 to push tab 66 toward cage 30. It should be noted that in all configurations described herein a fixation screw 46 could be used to press/push a cervical plate toward a cage 30 until the plate makes contact with a vertebral body. In the embodiments that include an elongated slot or blocks (FIGS. 12, 13, 15) a fixation screw 46 with knob 50 or head larger than the elongated slot or larger than the hole in the block could be used to push the plate toward the cage until the plate makes contact with a vertebral body.

In all embodiments disclosed herein, after mounting a plate to a cage 30 with a fixations screw 46 as described herein, self drilling screws may be used to mount plate 58 to a vertebrae. That is, self drilling screws may be inserted in eyelets 60 without first pre-drilling holes through eyelets 60 using a drill guide. It should be noted that in addition to the methods described here any other method or system may be employed to mount any cervical plate according to the present invention to a vertebrae without deviating from the present invention. That is, the present invention should not be limited to any particular method or system of mounting a plate according to the present invention to vertebrae. For example, a drill guide may be used which allows for mounting of a screw through an eyelet 60 through a cannula after drilling or even without drilling, whereby the drill guide is removed after the plate is first mounted to a vertebral body.

Plate 58 may also include a second projecting tab 65 with an eyelet 67, with similar or the same dimensions as eyelet 64. Second projecting tab 65 is located in a position opposite to tab 66 at another end of plate 58 projecting toward tab 66. Eyelet 67 may be further away from the lowest eyelets 60 than eyelet 65 is from the top eyelets 60. The difference between the positions of eyelets 67 and 64 would allow the surgeon to select which eyelet to use for mounting of plate 58 to cage, thereby allowing the surgeon to select how close eyelets 60 can be to the end plate.

It should be noted that while the mounting of a cervical plate is illustrated using a cage 30 between the top vertebra 10 and bottom vertebra 12, one could follow the same procedure using cage 30 between bottom vertebra 14 and middle vertebra 14 without deviating from the scope and spirit of the invention.

The examples disclosed above allow for a fixation point with a predetermined distance eyelets 60 of plate 58. The fixation point may be as illustrated, or may be part of the body of a cervical plate such as cervical plate 58. For example, cervical plate 58, instead of one or more projecting tabs with an eyelet may include a projecting tab with a male extension projecting away from the tab and configured (dimensioned) to be received in hole 38 of a cage 30.

Figure 11:
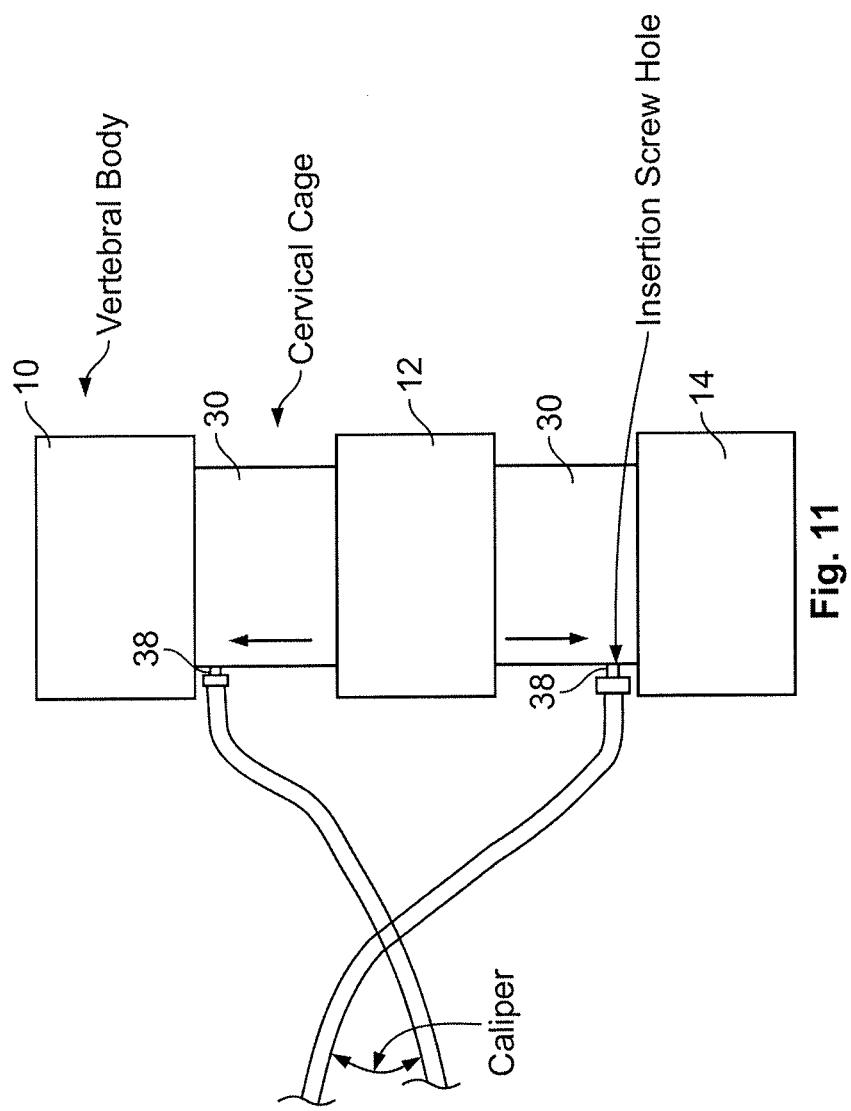
FIG. 11 illustrates that a caliper can be used to select the size of a cervical plate based on reference points on intervertebral cages located between adjacent intervertebras.

Furthermore, a surgeon may use a caliper or the like device to determine the distance between insertion holes 38 of two cages 30 as illustrated in FIG. 11, and select a cervical plate 38 that could provide ideal length and therefore mounting locations on the top vertebra 10 and bottom vertebra 14. This can be accomplished by reversing the orientation of cage 30, the cephaled cage having insertion hole 38 close to cephaled vertebral body, and the caudal cage having an insertion hole 38 close to caudal vertebral body. The measuring can span the length of three vertebral bodies or greater.

The attached appendix further summarizes the benefits of a system according to the present invention.

Figure 12:
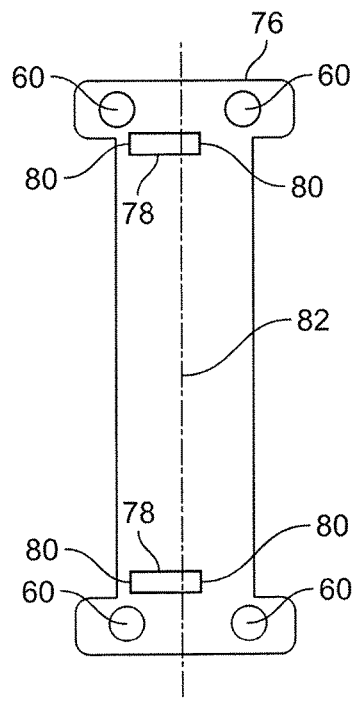
FIG. 12 depicts a front plan view of a cervical plate that can be used in a system according to another embodiment of the present invention.

Referring now to FIG. 12, a system according to another embodiment of the present invention could include a cervical plate 76, which, instead of an eyelet 64 (See FIG. 5), includes at least one elongated slot 78. Elongated slot 78 can be any shape, for example, rectangular or oblong. In the example shown in FIG. 12 two elongated slots 78 are provided, one closer to the top eyelets 60 near the top end of plate 76 and another near the bottom end of plate 76 closer to the bottom eyelets 60.

Preferably, each elongated slot 78 would be in position to set a proper distance between eyelets 60 and a screw hole 38 of a cage in the same manner as the cervical plate of the first embodiment described above. Each elongated slot 78 allows plate 76 to move laterally (side to side) when a screw 62 mounts cervical plate 76 to a cage through a slot 78.

In the example shown in FIG. 12, each elongated slot is off-centered, meaning that a center of each slot 78 located between its terminal ends 80 does not coincide with the central longitudinal axis 82 of cervical plate 76.

Plate 76, as illustrated, when fixed to a cage 30 by a fixation screw 46, for example, can be shifted laterally by sliding on fixation screw 46 from left to right allowing for adjustment in position. Plate 76 could be re-oriented 180 degrees (relative to the illustrated orientation) by the surgeon, mounted to a cage 30 with a fixation screw 46, and shifted laterally by sliding on fixation screw 46 from right to left.

Figure 13:
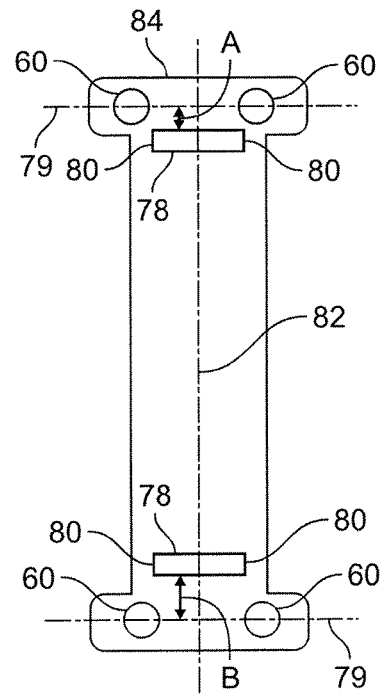
FIG. 13 depicts a front plan view of another variation of a cervical plate that can be used in a system according to another embodiment of the present invention.

FIG. 13 discloses another cervical plate 84. Cervical plate 84 includes all features of cervical plate 76 except that the center of each elongated slot 78 in cervical plate 84, as defined above, coincides with the central longitudinal axis of cervical plate 84. That is, elongated slots 78 are centered.

In use, each slot 78 could be positioned so that it registers with a screw hole 38 of a cage 30. As an additional feature, the distance A, B between the top edge of a slot 78 and a line 79 that crosses the centers of eyelets 60 could be different for each slot 78 in the plate shown in FIG. 13 or the plate shown in FIG. 12 thereby allowing the surgeon some flexibility in the use of the plate during an operation. That is, the distance A (FIG. 13) between top slot 78 and top eyelets 60 may be different than the distance B (FIG. 13) between bottom slot 78 and the bottom eyelets 60, allowing the surgeon to select the proper distance for the holes in a vertebral body and the position of the screws that fix the cervical plate relative to the end plate.

Figure 14A:
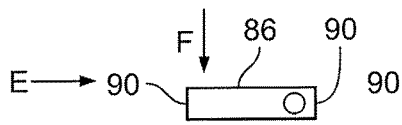
FIGS. 14A, 14B, 14C show a top plan view of examples of adapter blocks that can be used with cervical plates shown in FIGS. 12 and 13.
Figure 14B:
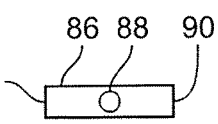
Figure 14C:
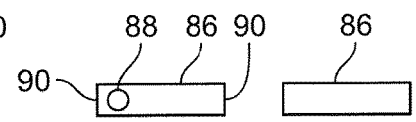
Figure 14D:
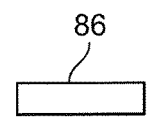
FIG. 14D is a side plan view of any of one of the blocks shown in FIGS. 14A, 14B, 14C.

Alternatively, each elongated slot 78 could be sized to receive an adapter block 86 as shown in FIGS. 14A, 14B, 14C. Each adapter block 86 could be a solid elongated body that is sized to be received tightly inside a respective elongated slot 78 such that, when received and in place, its surrounding peripheral wall makes intimate contact with the inner walls of a slot 78 and becomes restricted from sliding laterally or moving vertically in the slot (e.g. snap-fitted) relative to cervical plate 76, 84.

Each adapter block 86 includes at least one hole 88 that could be located centrally (FIG. 14B) between terminal ends 90 of each block 86, or off-center to the right (FIG. 14B) or the left (FIG. 14A) of the center of block 86. Either plate 76 or plate 84 could be used with an adapter block 86.

While slots 78 are shown to be straight and transverse to the longitudinal axis 82, it should not be understood that the present invention is restricted to such a configuration. A curved slot, overlapping semicircles (like seen in a clover leaf), or a slot oriented at an angle relative to longitudinal axis 82, which is not ninety degrees could be also be used to achieved different movements and translations.

Figure 15:
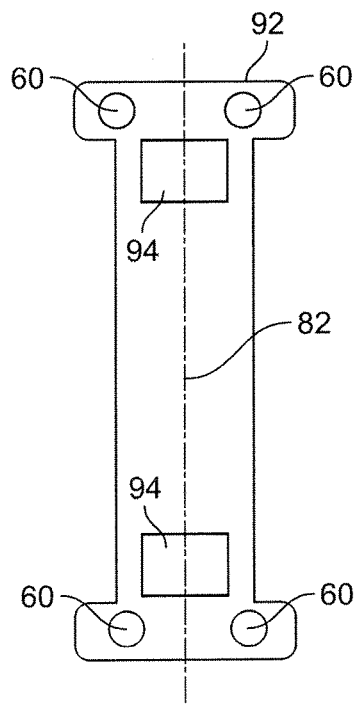
FIG. 15 depicts a front plan view of a cervical plate that can be used in a system according to a further embodiment of the present invention.
Figure 16A:
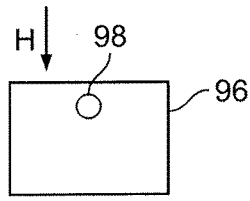
FIGS. 16A, 16B, 16C show a top plan view of examples of adapter blocks that can be used with a cervical plate shown in FIG. 15.
Figure 16B:
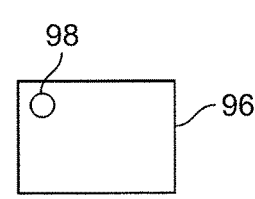
Figure 16C:
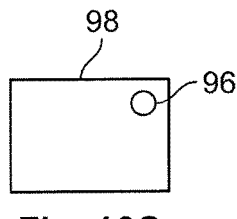
Figure 16D:
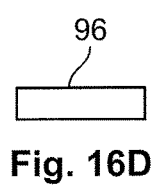
FIG. 16D is a side view of any one of the blocks shown in FIGS. 16A, 16B, 16C.

Referring now to FIG. 15, a cervical plate 92 could include, instead of an elongated slot 78 or two elongated slots 78 (centered (FIG. 13) or off-centered (FIG. 12)), at least one rectangular opening (window) 94 or more than one (e.g. two) rectangular windows 94. Each window 94 would be configured to receive a rectangular adapter block 96 as illustrated in FIGS. 16A, 16B and 16C. Each adapter block 96 would include at least one hole 98 to receive a screw 62 (see FIG. 5). As illustrated in FIGS. 16A-16C, a hole 98 could be located anywhere on the plate including locations away from the center of block 96, near a corner and so on.

Unlike block 86, block 98 is not elongated, but is tall and wide. To be more specific, while block 86 has a length between its terminal ends 90 that, as shown, is at least twice the diameter of a hole 88, its height is less than the diameter of two holes 88. That is, block 86 can only accommodate the possibility of two or more holes 88 along its longitudinal axis extending between its terminal ends 90, and no more than one hole 88 in a direction transverse to its longitudinal axis.

On the other hand, block 96 has a width that could accommodate two or more columns of holes 98, and has a height that could accommodate two or more rows holes 98. Consequently, block 96 has an area that provides available locations for holes 98 that would allow for the combination of lateral (side to side at a ninety degree angle to longitudinal axis) as well as vertical (up and down along longitudinal axis 82) positional adjustments of plate 92. Thus, the system of a cervical plate 92 and block(s) 96 allows for repositioning of plate 92 along a direction at any angle relative to a cage 30.

While blocks 86, 96 are shown with one hole 88, 98, it should be appreciated that blocks with multiple holes 88, 98, could be used with a plate 76, 84, 92 without deviating from the present invention.

Furthermore, while a rectangular blocks are shown, blocks of any shape could be used without deviating from the invention.

Each block 96 would be configured to be tightly received inside an opening 94 making intimate contact with the walls of opening 94 such that it would be restricted from movement parallel to longitudinal axis 82 and transverse to longitudinal axis 82.

Preferably, blocks 86 would have a shape and dimensions that corresponds to the shape and dimensions of opening 78 to obtain a tight fit.

Preferably, blocks 96 would have a shape and dimensions that correspond to the shape and dimensions of opening 94 to obtain a tight fit.

Figure 14E:
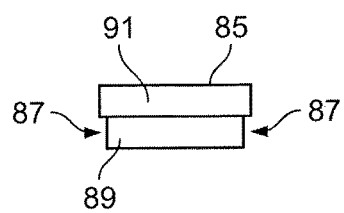
FIG. 14E depicts a side plan view of another variation of any one of the blocks shown in FIGS. 14A, 14B, 14C viewed in the direction of arrow E.
Figure 14F:
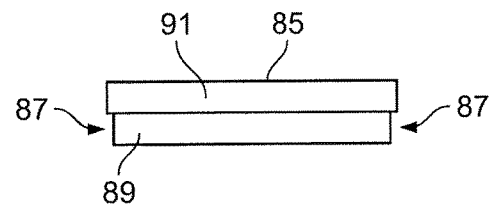
FIG. 14F depicts a side plan view of the variation of FIG. 14E in the direction of arrow F.

Referring now to FIGS. 14E and 14F, a block 85 could include a cutaway or recess 87 according to another variation. Recess 87, preferably, would be an endless and continuous recess around block 85. Recess 87 would define a first section 89 that is tightly received in a slot 78 as explained above, and a second section 91 that would cover a larger area than slot 78, whereby block 85 would be prevented from being fully received in a slot 78. That is, the ledge created by recess 87 would engage the surface surrounding slot 78 to restrict movement of block 85.

Figure 16E:
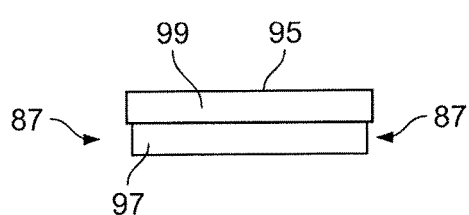
FIG. 16E depicts a side plan view of another variation of any one of the blocks shown in FIGS. 16A, 16B, 16C viewed in the direction of arrow G.
Figure 16F:
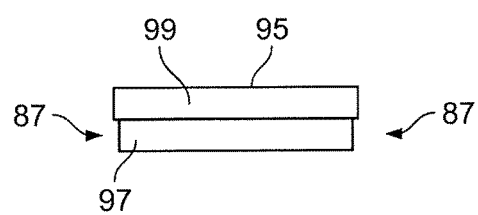
FIG. 16F depicts a side plan view of the variation of FIG. 16E in the direction of arrow H.

As illustrated in FIGS. 16E and 16F, block 95 could also include an endless and continuous recess 87 defining a first section 97 that is tightly received in an opening 94 as explained above and a second section 99 having an area larger than opening 99 to define a ledge that would make contact with the surface surrounding opening 94 to restrict movement of block 95 into opening 99.

Figure 14G:
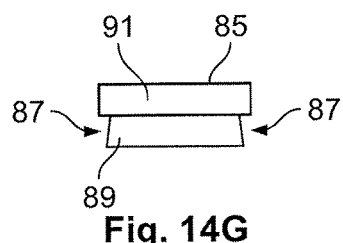
FIG. 14G depicts a side plan view of yet another variation of any one of the blocks shown in FIGS. 14A, 14B, 14C in the direction of arrow E.
Figure 14H:
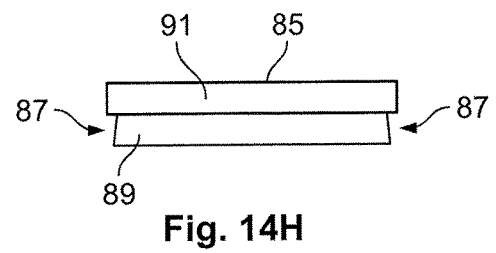
FIG. 14H depicts a side plan view of the variation of FIG. 14G in the direction of arrow F.

Referring to FIGS. 14G and 14H, recess 87 may have a wall that tapers (not vertical) that may help insertion of first section 89 into a slot.

Figure 16G:
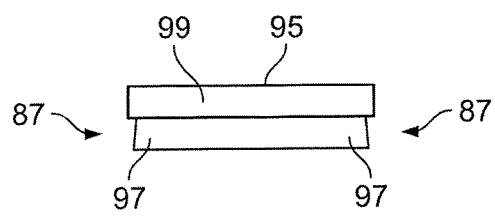
FIG. 16G depicts a side plan view of yet another variation of any one of the blocks shown in FIGS. 16A, 16B, 16C in the direction of arrow G.
Figure 16H:
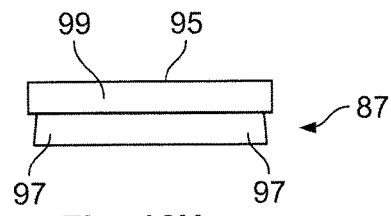
FIG. 16H depicts a side plan view of the variation of FIG. 16G in the direction of arrow H.

Referring to FIGS. 16G and 16H, recess 87 may have a wall that tapers (not vertical) that may help insertion of first section 97 into an opening 94.

It should be noted that first sections 89, 97 of blocks 85, 95 as shown in FIGS. 14G, 14H, 16G and 16H would still be large enough to make intimate contact with inner walls of a slot 78/an opening 94 to realize a tight fit as explained above.

To use plates 76, 84, 92, a modified fixation component 100 (FIG. 17) may be used that does not include anchor portions 54, 56, which are included with fixation component 44 shown in FIGS. 3A and 3B. In the variation shown in FIG. 17, anchor portions 54, 56 may be omitted while other features of fixation component 44 would be retained to realize fixation component 100.

Optionally, a spring 102 could be provided between knob 50 and elongated bar 52 to bias knob 50.

Figure 17:
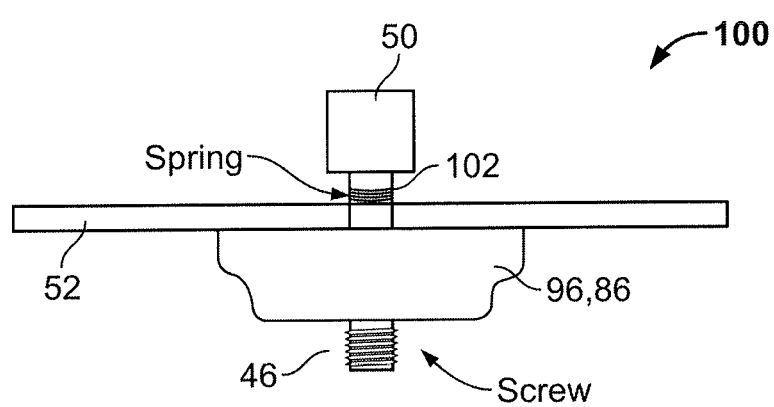
FIG. 17 depicts a top plan view of a fixation component for use with a system that includes any one of the cervical plates shown in FIGS. 12, 13 and 15.

FIG. 17 illustrates fixation screw 46 received in a hole, which could be hole 88, 98 of any one of the adapter blocks 86, 96 discussed above.

Fixation component 100 could be used with the drill guide shown in FIG. 6 instead of fixation component 44 to realize a system according to another embodiment of the present invention.

Figure 18A:
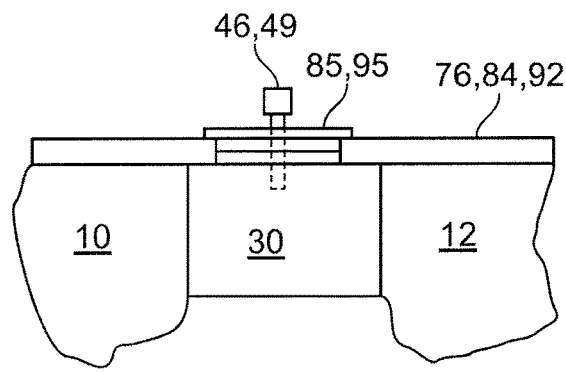
FIGS. 18A-18C illustrate the use of different blocks in mounting a cervical plate to a cage.
Figure 18B:
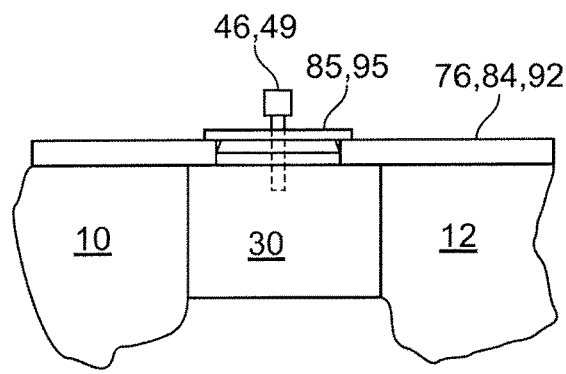

Referring to FIG. 18A, a block 85, 95 could be used to temporarily fix a cervical plate 76, 84, 92 to a cage using either a fixation screw 46 or a fixation pin 95. FIG. 18B illustrates using blocks 85, 95 having tapering-wall recesses 87 (FIGS. 14G, 14H, 16G, 16H). In both cases, fixation screw 46 could have an integrated spring 47 (FIG. 3C).

Figure 18C:
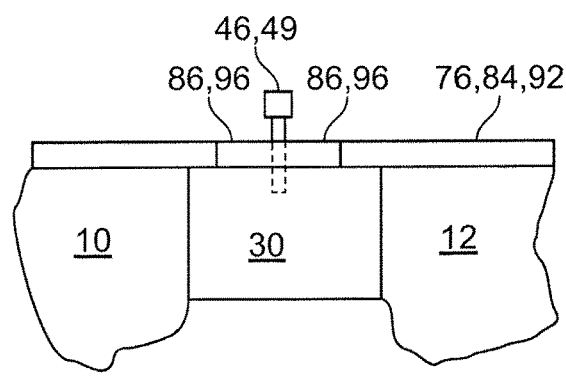

Referring to FIG. 18C, a block 86, 96 could be used to temporarily fix a cervical plate 76, 84, 92 to a cage 30 using either a fixation screw 46 or a fixation pin 95. When used, fixation screw 46 could be provided with an integrated spring 47.

Thus, the systems disclosed herein allow a threaded or non-threaded fixation hole in a cervical spine cage/allograft to serve as a fixation point for temporary attachment of a cervical plate herein in order to optimize the placement of the plate as it relates to the surrounding anatomy and to the cage.

The cervical plates disclosed include a feature that allows attachment to a fixation hole of a cage, and can be used with any and most forms of cervical locking mechanisms. The blocks, for example, allow for asymmetrical positioning of a cervical plate relative to a cage using the same fixation point associated with the cage. The adapter blocks would allow medial lateral translation and superior/inferior translation (FIG. 15). The asymmetrically (off-center) positioned slots allow cephaled/candal movement of a cervical plate possible.

The system with blocks can be used in two different ways.

First, a block can be secured/received in the corresponding slot of a plate, and then the block can be secured to a cage in the manner described (FIGS. 18A and 18B).

Second, a block can be first secured to a cage and the plate may be then coupled to the block by fitting the slot of the plate to the block (FIG. 18C). Once the procedure is over, the block could be removed. In this example, the slot would have to be wide enough to allow the block and the fixation screw to pass.

In another embodiment, a fixation screw could be devised with a stem that is receivable in a slot and is dimensioned to frictionally couple with the slot to allow for fine medial and lateral adjustment of the position of the slot. Such a fixation screw would be designed to be removed once the cervical plate is installed in place.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A system comprising an intervertebral cage and a cervical plate configured to be mounted to said intervertebral cage, said intervertebral cage having a front wall, the cervical plate comprising a body having a top edge, a bottom edge and two side edges, at least one top eyelet located along said top edge, at least one bottom eyelet located along said bottom edge, a mounting section located between said top eyelet and said bottom eyelet, the mounting section being configured to be mounted to a corresponding reference feature at said front wall of said intervertebral cage, said reference feature being located in a position to set a distance between one of said at least top eyelet and said at least bottom eyelet and an edge of said front wall to position at least one of said eyelets over a mounting location on a vertebra when said mounting section is mounted to said reference feature;

another mounting section configured to be mounted to said reference feature at said front wall of said intervertebral cage, said reference feature being located in a position to set another distance between one of said at least top eyelet and said at least bottom eyelet and an edge of said front wall to position at least one of said eyelets over a mounting location on a vertebra when said another mounting section is mounted to said reference feature, said another distance being different than said distance;

a fixation component that includes a screw receivable in an opening defined in said mounting section and a hole defined in said front wall to mount said cervical plate to said cage; and a drill guide having at least one cannula configured to register with at least one of said eyelets, wherein said fixation component is supported by said drill guide at a location spaced from said cannula, wherein said opening of said mounting section includes a slot and said another mounting section includes a slot.

2. A system according to claim 1, wherein said slots are off-centered.

3. A system according to claim 1, wherein each said slot has a center located between its terminal ends, which coincides with a central longitudinal axis of the cervical plate.

4. A system according to claim 1, wherein said slot of said mounting section includes a feature selected from a group consisting of an off-centered slot, and a centered slot, and said slot of said another mounting section includes a feature selected from a group consisting of an off-centered slot, and a centered slot.

5. A system according to claim 1, wherein said slot of said mounting section receives an adapter block having an opening therein to mount said cervical plate to said reference feature of said cage, and said slot of said another mounting section is configured to receive said adapter block.

6. A system according to claim 1, wherein said fixation component includes at least an anchor spaced from said opening and configured to be received in a corresponding slot defined in said front wall of said cage.

7. A system according to claim 1, wherein said fixation component includes two spaced anchors, wherein said anchors are either configured to be received in respective slots defined in said front wall of said cage, or spaced to grip said side edges of said body.

* * * * *